(12) United States Patent
Vachon et al.

(10) Patent No.: US 6,340,421 B1
(45) Date of Patent: Jan. 22, 2002

(54) MICROELECTROGRAVIMETRIC METHOD FOR PLATING A BIOSENSOR

(75) Inventors: David J. Vachon, Granada Hills; Jenn-Hann Wang, Van Nuys, both of CA (US)

(73) Assignee: MiniMed Inc., Sylmar, CA (US)

( * ) Notice: Subject to any disclaimer, the term of this patent is extended or adjusted under 35 U.S.C. 154(b) by 0 days.

(21) Appl. No.: 09/642,623

(22) Filed: Aug. 18, 2000

Related U.S. Application Data

(60) Provisional application No. 60/204,408, filed on May 16, 2000.

(51) Int. Cl.[7] ................................................ C25D 5/00
(52) U.S. Cl. ..................... 205/133; 205/136; 204/224 R
(58) Field of Search ................................. 205/133, 136; 204/224 R

(56) References Cited

U.S. PATENT DOCUMENTS

| 4,671,288 A | 6/1987 | Gough |
| 5,320,725 A | 6/1994 | Gregg et al. |
| 5,403,700 A | 4/1995 | Heller et al. |
| 5,540,828 A | 7/1996 | Yacynych |
| 5,777,060 A | 7/1998 | Van Antwerp |
| 5,786,439 A | 7/1998 | Van Antwerp |
| 5,965,380 A | 10/1999 | Heller et al. |

Primary Examiner—Kishor Mayekar
(74) Attorney, Agent, or Firm—Gates & Cooper LLP

(57) ABSTRACT

Disclosed is a method for microelectrogravimetrically depositing an electroactive species onto an electrode or a plurality of electrodes comprising dispensing a solution containing the electroactive species from a microdispenser to form a hanging drop of the solution and contacting the electrode with the hanging drop of the solution, wherein the electrode is electrically coupled with the microdispenser to form an electrochemical cell, and applying a potential to the electrochemical cell. The application of the potential effects deposition of the electroactive species onto the electrode. The method of the invention eliminates the need for immersion of the electrode in a bath, reduces the volume of solution required by a factor of at least 10–100, and avoids uneven depletion of various components of the solution over successive applications. The method reduce costs, provides increased reproducibility in the plating process and avoids contamination of the solution, and is particularly suited for plating of enzymes, such as glucose oxidase, or metals, such as platinum, onto electrodes for use as biosensors.

26 Claims, 3 Drawing Sheets

MICROELECTROGRAVIMETRIC METHOD FOR PLATING A BIOSENSOR

This application claims the benefit, under 35 U.S.C. 119(e), of U.S. provisional apllication Ser. No. 60/204,408, filed May 16, 2000.

TECHNICAL FIELD OF THE INVENTION

This invention relates generally to the manufacture of biosensor electrodes.

BACKGROUND OF THE INVENTION

An enzyme electrode is a biomedical sensor that can be used to determine the concentration of certain biochemicals rapidly and with considerable accuracy. Enzyme electrodes are used to detect glucose, urea, uric acid, various alcohols, and a number of amino acids when used in certain well-defined situations.

Glucose sensors suitable for in vivo use can be prepared by depositing a glucose sensitive enzyme, such as glucose oxidase, onto an electrode via an electromotive plating process. The substrate is immersed in a bath comprising glucose oxidase, a stabilizing protein, a surfactant and a buffer for conductivity and stability of the protein solution. The enzyme is deposited onto the electrode potentiometrically.

Such methods require considerable volumes of solution for immersion of the electrodes and can result in protein contamination of counter or reference electrodes if present in the array, which, in turn, leads to signal interference. In addition, the concentrations of solution components can vary over a series of electrode immersions and plating cycles from the same bath. There is thus a need for improved methods of plating enzyme onto electrodes that can provide greater efficiency and reproducibility in the plating process, as well as providing adaptability to automated plating processes.

SUMMARY OF THE INVENTION

To overcome the limitations in the prior art described above, and to overcome other limitations that will become apparent upon reading and understanding the present specification, the invention provides a method for depositing an electroactive species onto an electrode. In one embodiment, the method comprises partially dispensing a solution containing the electroactive species from a microdispenser so as to form a hanging drop of the solution. The method further comprises contacting the electrode with the hanging drop of the solution, wherein the electrode is electrically coupled with the microdispenser so as to form an electrochemical cell, and applying a potential to the electrochemical cell. The application of the potential results in deposition of the electroactive species onto the electrode.

In yet another embodiment, a microdispensing device, such as a BioJet®, may be used to deposit a fine bead of conductive plating solution on the first or "working electrode" thus avoiding contact with the reference or counter electrodes in the sensor configuration. This method further comprises placing one or more electrodes into the bead and applying a potential to the electrochemical cell. This type of microdispensing device can be readily adapted for automation of the method for plating a plurality of working electrodes, providing efficiency of both time and costs, as well as a high degree of accuracy.

The method of the invention eliminates the need for immersion of the electrode in a bath, reduces the volume of solution required by a factor of at least 10–100, and avoids uneven depletion of various components of the solution over successive applications. The method reduces costs, provides for increased reproducibility in the plating process and avoids contamination of the solution. Because of the direct placement of solution onto the electrode and greater control over the deposition as a consequence of current density, a smaller amount of stabilizing protein is required, resulting in greater activity and reduced plating times.

In one embodiment, the invention provides an apparatus for depositing an electroactive species onto an electrode. The apparatus comprises a microdispenser capable of dispensing a solution containing the electroactive species so as to form a hanging drop of the solution, an electrode holder capable of placing the electrode in electrical contact with the microdispenser so as to form an electrochemical cell, and a potentiometer disposed between the microdispenser and the electrode holder. Examples of electroactive species include, but are not limited to, enzymes, such as glucose oxidase, lactate oxidase, and amino acid oxidase, as well as metallic solutions, such as a platinum salt (e.g., hydrogen hexachloroplatinate) solution.

In one embodiment, the apparatus is used for depositing an electrode surface, such as platinum black onto a conductive metal substrate such as gold, nickel, platinum, iridium or other suitable metal material. The solution to be microdispensed contains an appropriate metal salt or organometallic compound and forms a bead or drop to be deposited onto an electrode. The electrode holder is used to place an inert electrode in electrical contact with the solution drop or bead, and a potentiometer is disposed between the microdispenser and the electrode so as to form an electrochemical cell.

DETAILED DESCRIPTION OF THE PREFERRED EMBODIMENT

In the following description of the preferred embodiment, reference is made to the accompanying drawings, which form a part hereof, and in which is shown by way of illustration a specific embodiment in which the invention may be practiced. It is to be understood that other embodiments may be utilized and structural changes may be made without departing from the scope of the present invention.

Overview

The present invention provides a method and apparatus for depositing an electroactive species onto an electrode or metal substrate that eliminates the need for immersion of the electrode in a bath, reduces the volume of solution required by a factor of at least 10–100, and avoids uneven depletion of various components of the solution over successive applications. The method can reduce costs, provide for increased reproducibility in the plating process and avoid contamination of the solution via direct placement of solution onto the electrode or metal substrate of interest, and greater control over the deposition as a consequence of current density. In the case of enzyme plating, a smaller amount of stabilizing protein can be used when depositing an enzyme thus resulting in greater activity, better adhesion, and reduced plating times compared to methods requiring immersion.

The method of the invention comprises contacting a first electrode with a hanging drop or deposited bead of a solution comprising an electroactive species, wherein the first electrode is electrically coupled with the microdispenser so as to form an electrochemical cell. As used herein, "electroactive species" means any electrochemcially active or electromotively mobile species, including enzymes, other proteins and metallic solutions. In one embodiment, the first electrode comprises the microdispenser. The method further comprises applying a potential to the electrochemical cell. The contacting can be achieved by partially dispensing a solution containing the electroactive species from a microdispenser so as to form a hanging drop of the solution. The application of the potential, e.g., an electrical current or voltage, results in deposition of the electroactive species onto the electrode.

In yet another example, a continuous bead of plating solution is drawn/deposited across an array of electrodes to be plated, using an automated microdispensing apparatus. For example, a series of electrodes can be moved on a conveyor as plating solution is deposited on the electrodes as they pass the microdispenser. A counter electrode is inserted into the bead of plating solution to complete the electrochemical cell, and an appropriate plating current/voltage is applied.

Electrode Array

Figure 1A:
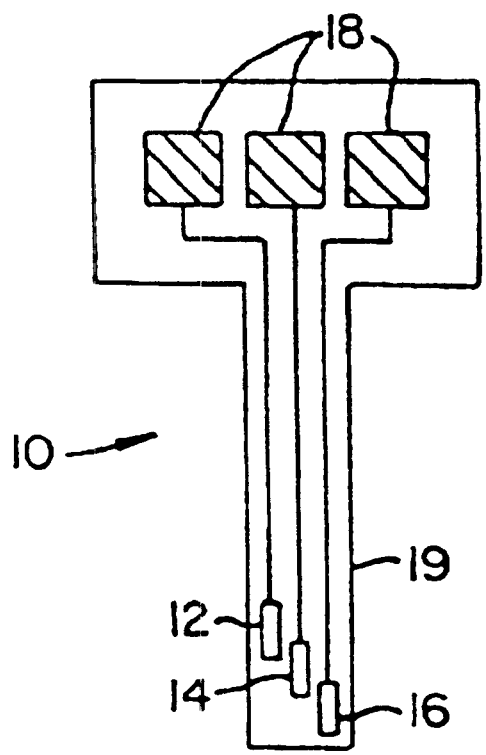
FIG. 1A is a schematic top view of a sensor comprising an electrode prepared in accordance with the present invention.
Figure 1B:
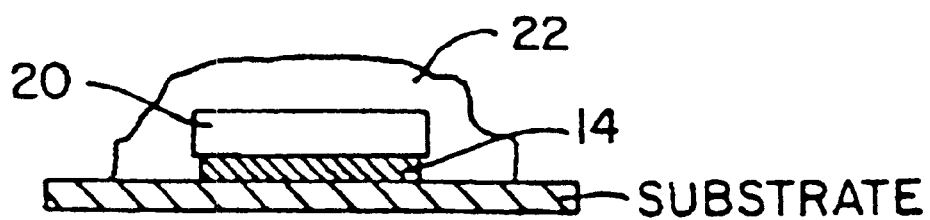
FIG. 1B is a sectional side view of a working electrode prepared in accordance with the present invention.

FIG. 1 illustrates an exemplary sensor 10 comprising a working electrode 14 plated with an enzyme in accordance with the invention. As shown in FIG. 1A, a sensor 10 can have a reference electrode 12, a working electrode 14, and a counter electrode 16 deposited on a polymeric sheet 19. The sensor 10 further comprises a series of bonding pads 18. FIG. 1B shows a cross-sectional view of the working electrode 14 covered with a layer 20 of an enzyme, such as glucose oxidase. The entire electrode array can then be coated with a layer 22 of a polymer. The electrodes can be made of any conductive surface, e.g., gold, platinum, palladium, chromium, copper, aluminum, pyrolitic carbon, composite material (e.g., metal-polymer blend), nickel, zinc, titanium, or an alloy, such as cobalt-nickel-chromium, or titanium-aluminum-vanadium, which is deposited on any of a variety of suitable materials, including glass, polyimide or polyester. In some embodiments, the electrode array comprises a flex-circuit layout/design. Of course, those skilled in the art will recognize that variations of the above components, and other types of electrodes can be used in the method of the invention.

Microelectrogravimetric Plating Apparatus

Figure 2:
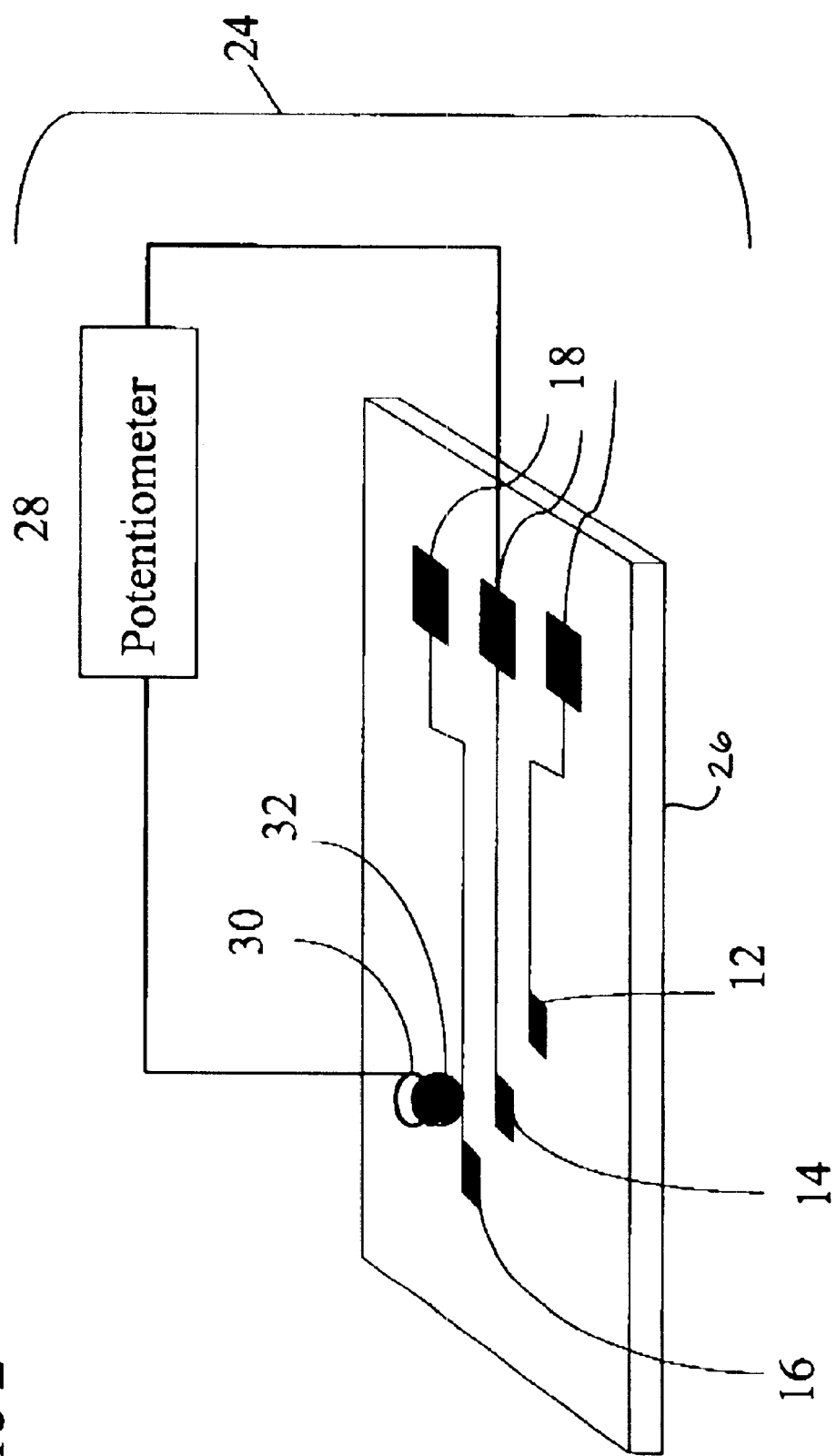
FIG. 2 illustrates an exemplary apparatus that could be used to implement the present invention.

FIG. 2 illustrates an exemplary apparatus 24 for performing the microelectro-gravimetric plating method of the invention. One or more sensors 12, 14, 16 are placed onto an electrode holder, such as a platform 26, and the working electrode 14 is connected to a potentiometer or current box 28, thus defining the anode of an electrochemical cell. The other half of the cell is provided by a microdispenser 30 or external electrode, preferably made of platinum or other inert metal. The microdispenser/external electrode 30 is capable of dispensing small volumes, preferably in the range of 0.5 to 5 μl. Examples of microdispensers/external electrodes 30 include, but are not limited to, a small loop, needle or micropipette. In some embodiments, the second half of the electrochemical cell is part of a flex-circuit layout/design. The apparatus can optionally further comprise a pipette volume controller, electronically controlled syringe, or similar means for controlled delivery of solution to the microdispenser 30. Of course, those skilled in the art will recognize that various combinations, arrangements and modifications of the above components can be used to accomplish the method of the invention.

Figure 3:
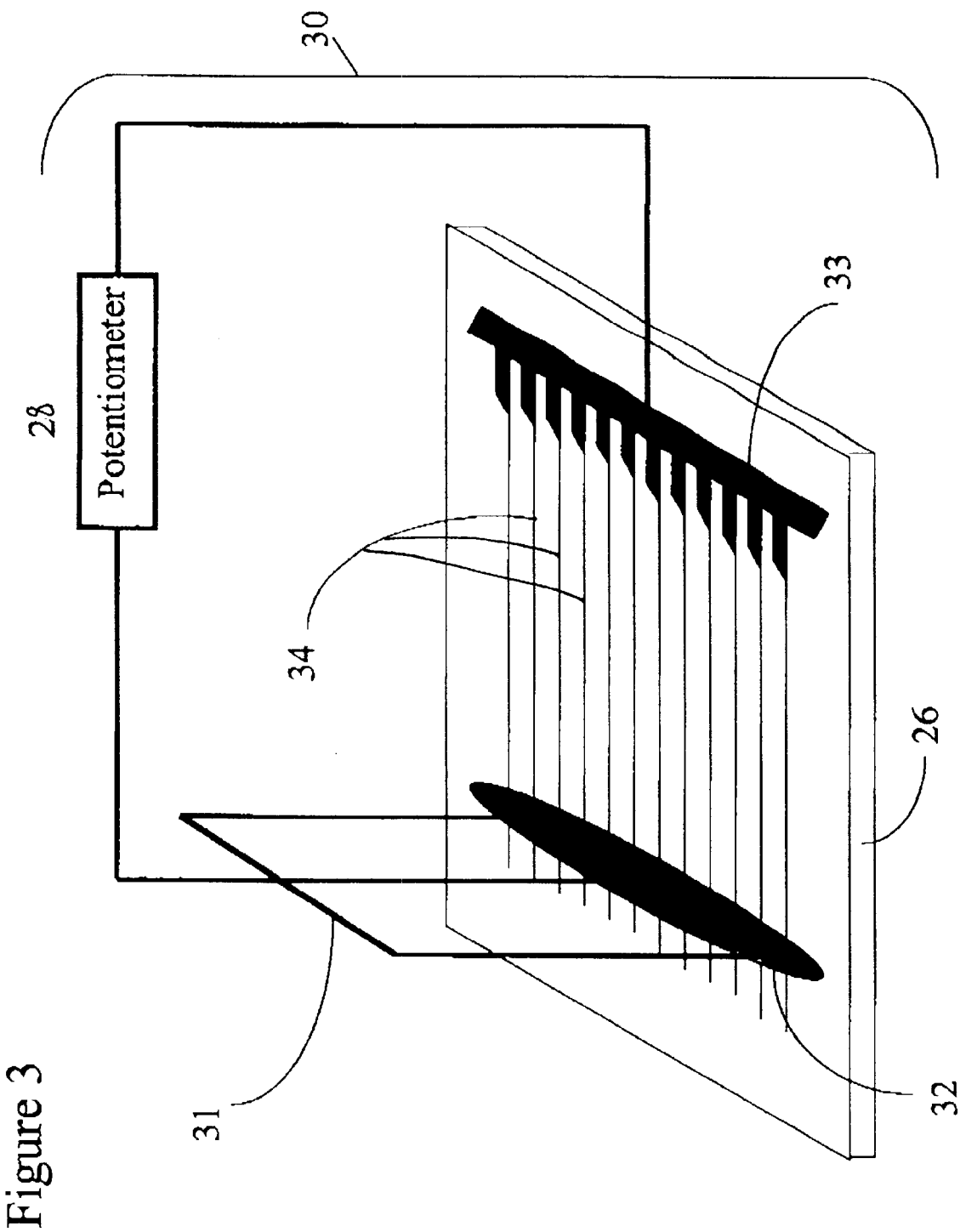
FIG. 3 illustrates an exemplary apparatus for simultaneous deposition of solution onto multiple sensors.

FIG. 3 illustrates an additional exemplary apparatus 30 that can be used for simultaneous deposition of solution 32 onto multiple sensors 34. A plurality of sensors 34 are placed onto an electrode holder, such as a platform 26, and connected via an electrode connector 33 to a potentiometer or current box 28. The potentiometer 28 is, in turn, connected to one or more microdispensers/electrodes 31 that are capable of dispensing small volumes onto the sensors 34.

Microelectrogravimetric Plating Method

The microdispenser 30 is loaded with an electroactive species, such as an enzyme solution/electrolyte or other electrochemically active solution. A drop 32 of solution is dispensed, e.g., via a pipette volume controller, so as to hang from the microdispenser 30 via surface tension. The drop 32 is brought into contact with the working electrode 14. This contact between the drop 32 and the working electrode 14 completes the circuit and voltage or current can be applied before or after the drop 32 contacts the working electrode 14. In such embodiments in which current is passed through the microdispenser 30, the microdispenser 30 preferably comprises a platinum tip. Working volumes of solution for plating a single electrode are in the range of about 0.5 to about 20 microliters. In another example, a bead of plating solution is drawn across one or more electrodes of interest and a second or counter electrode is placed in contact with the solution in order to complete the cell. Current can then be applied through the counter electrode.

The current applied can be delivered as a single pulse or as a sequence of pulses. Typically, the current is preferably applied for about 5 to about 60 seconds or for a period of minutes, and has an amperage of about 5 to about 50 μA. Illustrative current profiles are presented in the examples below. The current profile is selected to optimize activity of the deposited solution. The voltage will typically range from about 0.05 to about 15 volts, depending on the plating solution. Preferably, the current has a density of about 5 to about 25 mA/cm$^2$; more preferably, about 10 to about 20 mA/cm2.

For plating with an enzyme solution, the current is preferably about 5 to about 50 μA, more preferably about 15 to about 30 μA, and is applied for about 30 to about 60 seconds. Higher current (e.g., greater than about 30 μA) facilitates deposition of a thicker layer of enzyme solution. Very high current (e.g., greater than about 35 μA), however, can result in considerable air bubble formation inside the deposited enzyme layer. For enzyme plating, the voltage is preferably about 0.05 to about 9 volts, more preferably about 0.15 to about 0.5 volts.

For platinum plating, the current preferably ranges from about 20 to about 620 μA, more preferably about 45–50 μA, and may be applied for about 2 minutes. The application time can be varied depending on the desired thickness of the coating. The preferred voltage for this purpose is about 5 to about 15 volts, more preferably about 8–10 volts. The method can additionally be adapted to accommodate a plurality of sensors 34, as exemplified by the illustration in FIG. 3.

Enzyme Solution

Although a variety of enzyme solutions can be used in accordance with the invention, a typical solution contains the enzyme of interest, a stabilizing protein, a surfactant and a buffer. A preferred enzyme is glucose oxidase. Other enzymes of interest include, but are not limited to, lactate oxidase, amino acid oxidase, glutathione, and reductase. Examples of a stabilizing protein include, but are not limited to, albumin, such as ovalbumin or bovine serum albumin, fibrinogen, gelatin and lysozyme. Gelatin can also be used as a stabilizer. Examples of surfactant include, but are not limited to, Tweens, polyethylene glycols and their esters, polypropylene glycols and their esters, mixed polypropylene-ethylene glycols and their esters, and benzalkonium salts. Examples of wetting agents and emulsifying agents include, but are not limited to, Tweens 20–80, glycerol and fatty acids. A typical buffer is phosphate buffered saline, pH 7.4. Illustrative formulations are presented in the examples below.

Additional coatings can be applied to optimize use of the electrode as a biosensor in accordance with the desired use. For example, U.S. Pat. Nos. 5,777,060 and 5,786,439 describe coatings suitable for use with biosensors, particularly for use with glucose oxidase and glucose detection.

Platinum Plating Solution

Other plating solutions can be developed for other electroactive or electromotively mobile species to be plated onto electrodes. For example, metals and other proteins, in addition to enzymes, can be used for plating in accordance with the invention. In particular, electrodes plated with platinum black are useful, and can be prepared using platinum salt solutions such as the hydrogen hexachloroplatinate solution described in the examples below.

Examples

The following examples are presented to illustrate the present invention and to assist one of ordinary skill in making and using the same. The examples are not intended in any way to otherwise limit the scope of the invention.

Example 1

Current Profiles for Plating

A variety of current profiles were tested for plating of electrodes with a glucose oxidase solution. A small amount (0.5–10 $\mu$L/sensor) of enzyme plating solution containing about 6.25 wt. % glucose oxidase, 4.5 wt. % bovine serum albumin (BSA) and 0.1 wt. % Tween 40 in phosphate buffered saline (PBS), pH 7.4, was applied to 12 working electrodes using a micropipette/microdispenser (BioJet™ from BioDot Inc.). A controlled current box and a counter electrode of platinum wire were used to immobilize the enzyme solution onto the working electrode. The results were assessed by soaking the sensor in 100 mg/dL glucose solution and recording the output current. The results for individual profiles tested are presented below. For pulse sequences, the time between pulses was 0 seconds. The plating system has a built-in 10 K ohm resistor. When 10 $\mu$A of current was applied to the electrodes, the potential between positive and negative electrodes was 0.1 volt.

| Profile | | Results |
|---|---|---|
| 1 Current ($\mu$A) | 10 | deposit a very thin layer of GOx/BSA |
| Time (sec) | 60 | |
| 2 Current ($\mu$A) | 15 | deposit a very thin layer of GOx/BSA, small air bubbles was trapped inside the deposit layer |
| Time (sec) | 60 | |
| 3 Current ($\mu$A) | 20 | deposit a thin layer of GOx/BSA, small air bubbles |
| Time (sec) | 60 | |
| 4 Current ($\mu$A) | 25 | deposit a thicker layer of GOx/BSA, medium size air bubbles |
| Time (sec) | 60 | |
| 5 Current ($\mu$A) | 30 | deposit a thick layer of GOx/BSA, big air bubble |
| Time (sec) | 60 | |
| 6 Current ($\mu$A) | 5  25 | deposit a thick layer of GOx/BSA, smooth coating, no air bubble |
| Time (sec) | 30  60 | |

| Profile | | | | | | | Results |
|---|---|---|---|---|---|---|---|
| 7 Current ($\mu$A) | 5 | 35 | | | | | deposit a thick layer of GOx/BSA, smooth coating, no air bubble |
| Time (sec) | 30 | 60 | | | | | |
| 8 Current ($\mu$A) | 12 | 30 | 35 | 31 | 21 | 17 | |
| Time (sec) | 7 | 11 | 9 | 13 | 15 | 24 | deposit a thick layer of GOx/BSA, no air bubble, pre-membrane activity test result: ~189 nA (in 100 mg/dl glucose solution) |
| 9 Current ($\mu$A) | 5 | 15 | 35 | 0 | | | |
| Time (sec) | 30 | 20 | 40 | 240 | | | deposit a thick layer of GOx/BSA, pre-membrane activity test result: ~200 nA (in 100 mg/dl glucose solution) |
| 10 Current ($\mu$A) | 5 | 35 | 10 | 35 | 10 | 35 | |
| Time (sec) | 25 | 15 | 5 | 15 | 5 | 15 | deposit a thick layer of GOx/BSA, few medium size air bubbles |
| 11 Current ($\mu$A) | 5 | 25 | 40 | 1 | | | |
| Time(sec) | 10 | 10 | 60 | 240 | | | deposit a thick layer of GOx/BSA, pre-membrane activity test result: ~250 nA (in 100 mg/dl glucose solution) |
| 12 Current ($\mu$A) | 5 | 25 | 40 | 1 | 1 | 1 | 1 |
| Time (sec) | 10 | 10 | 60 | 60 | 60 | 60 | 0 |
| | | | | | | | deposit a thick layer of GOx/BSA, pre-membrane activity test result: ~295 nA (in 100 mg/dl glucose solution) |
| 13 Current ($\mu$A) | 5 | 15 | 35 | 5 | 15 | 35 | 5  30 |
| Time (sec) | 10 | 10 | 12 | 10 | 10 | 12 | 10  10 |
| | | | | | | | deposit a thick layer of GOx/BSA, pre-membrane activity test result: ~240 nA (in 100 mg/dl glucose solution) |

The results indicate that a preferred current profile is profile # 12, because it gives a thick deposit layer of GOx/BSA and higher enzymatic activity. These results also indicated that the thickness of the deposit GOx/BSA layer is greater with increased applied current (or potential, voltage). A smooth, thick, and air bubble-free coating can be obtained when the profile is started with the low current or potential first, then followed by a relatively high current or potential. The method is also advantageous because the resulting sensors have lower current readings or offset in an electrolyte solution (e.g., PBS without glucose), facilitating calibration.

Example 2

Enzyme Solutions

A typical enzyme plating solution contains glucose oxidase, albumin and Tween 40 in the pH 7.4 phosphate buffer saline. It has been reported that a solution containing 5% albumin and 5% glucose oxidase gives the highest activity. This example describes how the properties (i.e., activity, adhesion, thickness) of the deposited glucose oxidase (GOx) layer can be altered by changing the formulation of the GOx/albumin solution. The following formulations are some examples.

| Formulation of plating solution | Results |
|---|---|
| 1. GOx (6.25%)<br>Fibrinogen (4.5%)<br>Tween 40 (0.1%)<br>PBS (89.15%) | Thin layer of GOx/fibrinogen |
| 2. GOx (6.25%)<br>BSA (bovine serum albumin; 4.5%)<br>Tween 40 (0.1%) | Thick layer of GOx/BSA<br>The surface of deposited layer is very smooth. |

-continued

| Formulation of plating solution | Results |
| --- | --- |
| PBS (89.15%) | Pre-membrane activity test result: ~295 nA (in 100 mg/dl glucose solution) |
| 3. GOx (6.22%)<br>BSA (4.48%)<br>Tween 40 (0.1)<br>Polyethylene glycol-8000 (0.5%)<br>PBS (88.70%) | Thick layer of GOx/BSA Rough surface with some embedded particles, pre-membrane activity test result: ~255 nA (in 100 mg/dl glucose solution) |
| 4. GOx (5.6%)<br>BSA (4.1%)<br>Tween 40 (0.09%)<br>Gelatin (0.69%)<br>PBS (89.52) | Very thick layer of GOx/BSA, the surface of deposited layer is very rough, many big particles were embedded inside the layer. Pre-membrane activity test result: ~350 nA (in 100 mg/dl glucose solution |
| 5. GOx (6.25%)<br>Ovalbumin (4.5%)<br>Tween 40 (0.1%)<br>PBS (89.15%) | Thin layer of GOx/BSA The surface of deposited layer is not very smooth. |
| 6. GOx (6.25%)<br>Poly(sodium 4-styrenesulfonate) (0.08%)<br>PBS (93.67%) | Thin layer of GOx |

The results indicate that preferred formulations are formulations 2 and 4 above. The gelatin containing plating solution (formula 4) showed the highest enzymatic activity. Gelatin binds GOx molecules and BSA molecules together, so the GOx would not be washed away during the rinsing step (one step following the enzyme plating step). One reason for adding the Tween 40 in plating solutions is to increase the thickness of the deposited layer. Tween 40 serves as a good wetting agent.

Example 3

Platinum Plating

A platinum plating solution of 0.072 M hydrogen hexachloroplatinate and 0.00013 M lead acetate trihydrate in deionized water was applied using 9 volts and 46 $\mu$A for 2 minutes. Excellent plating of electrodes with platinum was obtained. The high quality of the platinum coating was confirmed via scanning electron microscopy.

The foregoing description of preferred embodiments of the invention has been presented for the purposes of illustration and description. It is not intended to be exhaustive or to limit the invention to a precise form disclosed. Many modifications and variations are possible in light of the above teaching. It is intended that the scope of the invention be limited not by this detailed description, but rather by the claims appended hereto.

What is claimed is:

1. A method for depositing an electroative species onto a electrode, the method comprising:
   (a) dispensing a solution the electroative species from a microdispenser to from a hanging drop of the solution;
   (b) contacting the first electrode with the hanging drop of solution, wherein the first electrode is electrically coupled with the microdispenser to form an electrochemical cell; and
   applying an electrical current to the electrochemical cell, wherein the application of the current effects deposition of the electroative species onto the electrode.

2. The method of claim 1, wherein the applying of (c) comprises placing a second electrode into contact with the drop.

3. The method of claim 2, wherein the second electrode comprises a wire loop or a needle.

4. The method of claim 2, wherein the second electrode comprises platinum.

5. The method of claim 1, wherein the microdispenser comprises a pipette.

6. The method of claim 1, wherein the first electrode comprises gold, platinum, palladium, chromium, copper, aluminum, nickel, zinc, titanium, cobalt-nickel-chromium alloy, or titanium-aluminum-vanadium alloy.

7. The method of claim 1, wherein the first electrode comprises a plurality of sensors.

8. The method of claim 1, wherein the current has a density of about 5 to about 25 mA/cm$^2$.

9. The method of claim 8, wherein the current has a density of about 10 to about 20 mA/cm$^2$.

10. The method of claim 1, wherein the electroactive species comprises a metal salt.

11. The method of claim 10, wherein the metal salt comprises hydrogen hexachloroplatinate.

12. The method of claim 10, wherein the current is about 20 to about 60 $\mu$A, and the voltage is about 5 to about 15 volts.

13. The method of claim 12, wherein the current is about 45 to about 50 $\mu$A, and the voltage is about 8 to about 10 volts.

14. The method of claim 1, wherein the electroactive species comprises an enzyme.

15. The method of claim 14, wherein the enzyme comprises glucose oxidase, lactate oxidase or amino acid oxidase.

16. The method of claim 14, wherein the current is about 5 to about 50 $\mu$A, and the voltage is about 0.05 to about 9 volts.

17. The method of claim 16, wherein the current is about 15 to about 30 $\mu$A, and the voltage is about 0.15 to about 0.5 volts.

18. The method of claim 14, wherein the current applying of (c) comprises applying a series of current pulses.

19. The method of claim 18, wherein the series of current pulses comprises applying current pulses of increasing amperage.

20. The method of claim 19, wherein the current pulses are about 5 to about 40 $\mu$A.

21. The method of claim 14, wherein the solution comprises gelatin or albumin.

22. The method of claim 1, wherein the solution comprises a stabilizing protein, a surface active agent, an emulsifying agent, and a buffer.

23. The method of claim 22, wherein the stabilizing protein comprises albumin.

24. The method of claim 1, wherein the dispensed solution has a volume of about 0.5 to about 50 $\mu$l.

25. The method of claim 1, wherein the dispensed solution has a volume of about 0.5 to about 10 $\mu$l.

26. An apparatus for depositing an electroative species onto an electrode, the apparatus comprising:
   (a) a microdispenser capable of dispensing a solution containing the electroative species to form a hanging drop of the solution;
   (b) an electrode holder capable of placing the electrode in electrical contact with the microdispenser to form an electrochemical cell; and
   (c) a potentiometer disposed between the microdispenser and the electrode holder.

* * * * *